United States Patent
Chuang

(10) Patent No.: US 10,059,682 B1
(45) Date of Patent: Aug. 28, 2018

(54) ASYMMETRIC DIANHYRDRIDES AND METHODS OF MAKING THE SAME

(71) Applicant: The United States of Americas as represented by the Administrator of NASA, Washington, DC (US)

(72) Inventor: Chun-Hua Chuang, Brecksville, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 15/722,038

(22) Filed: Oct. 2, 2017

Related U.S. Application Data

(60) Provisional application No. 62/402,122, filed on Sep. 30, 2016.

(51) Int. Cl.
| | | |
|---|---|---|
| *C07D 307/89* | (2006.01) | |
| *C08L 79/08* | (2006.01) | |
| *C08G 73/10* | (2006.01) | |
| *C07D 209/48* | (2006.01) | |

(52) U.S. Cl.
CPC ......... *C07D 307/89* (2013.01); *C07D 209/48* (2013.01); *C08G 73/1017* (2013.01); *C08L 79/08* (2013.01)

(58) Field of Classification Search
CPC .................................................. C07D 307/89
USPC ...................................................... 549/241
See application file for complete search history.

(56) References Cited

U.S. PATENT DOCUMENTS

| | | | |
|---|---|---|---|
| 6,716,270 B2 | 12/2004 | Ding et al. | |
| 6,979,490 B2 | 12/2005 | Steffier | |
| 7,015,304 B1 * | 3/2006 | Chuang ................ | C07D 307/89 264/45.1 |
| 7,250,545 B2 | 7/2007 | Roman et al. | |
| 7,381,849 B1 * | 6/2008 | Chuang ................ | C07D 307/89 562/407 |
| 7,425,650 B1 * | 9/2008 | Chuang ................... | C07C 51/06 562/480 |
| 8,093,348 B1 * | 1/2012 | Chuang ................ | C07D 307/89 528/271 |
| 8,993,710 B1 * | 3/2015 | Chuang ................... | C08L 79/08 528/271 |
| 2012/0190802 A1 | 7/2012 | Poe et al. | |
| 2014/0135447 A1 | 5/2014 | Golba et al. | |
| 2015/0045481 A1 | 2/2015 | Kim et al. | |

* cited by examiner

*Primary Examiner* — Taofiq A Solola
(74) *Attorney, Agent, or Firm* — Robert H. Earp, III; William M. Johnson

(57) ABSTRACT

A method for preparing asymmetric 3,4'-(hexafluroisopropylidene) dipthalic anhydride (a-6FDA) and asymmetric 3,4'-(methylene)diphthalic anhydride (a-MDPA) from asymmetric 2,3,3',4'-benzophenone dianhydride (a-BTDA). First, a-BTDA is converted to its corresponding N-alkyl or N-phenyl bisimides by reacting with either methylamine or aniline. The sequential addition of two trifluoromethyl ($CF_3$) groups to the carbonyl unit of a-BTDA produce the corresponding bisimides of asymmetric 6FDA, which is hydrolyzed to the asymmetric 6F-tetracarboxylic acid followed by cyclodehydration to obtain asymmetric 6F-dianhydride (a-6FDA). Separately, the carbonyl unit of bisimides of a-BTDA is reduced to a methylene unit to afford the corresponding bisimides of asymmetric 3,4'-(methylene)diphthalic anhydride, which is hydrolyzed to the asymmetric methylene tetracarboxylic acid followed by cyclodehydration to obtain 3,4'-(methylene)diphthalic anhydride (a-MDPA).

20 Claims, 1 Drawing Sheet

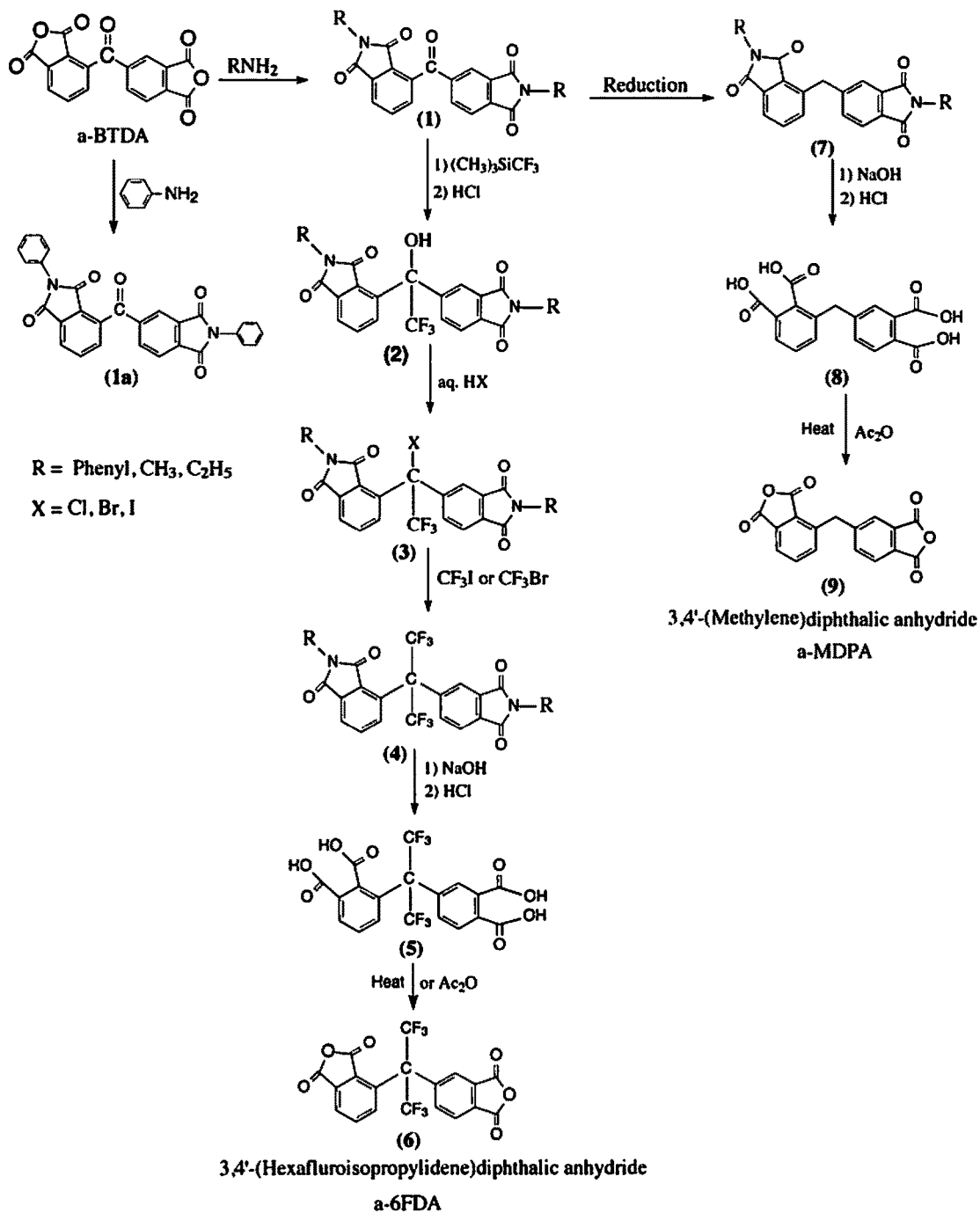
Synthesis of asymmetric dianhydrides from asymetric benzophenone dianhydride (a-BTDA)

ASYMMETRIC DIANHYRDRIDES AND METHODS OF MAKING THE SAME

CROSS-REFERENCE TO RELATED APPLICATIONS

This application claims the benefit of U.S. Provisional Patent Application Ser. No. 62/402,122 entitled "Synthesis of Asymmetric 6F-Dianhydride and 3,4'-(Methylene)Diphthalic Anhydride From Asymmetric Benzophenone Dianhydride" filed on Sep. 30, 2016, the entirety of which is incorporated by reference herein.

ORIGIN OF THE INVENTION

The invention described herein was made by an employee of the United States Government and may be manufactured and used by of for the Government for Government purposes without the payment of any royalties thereon or therefore.

TECHNICAL FIELD

The innovation relates generally to processes for the synthesis of asymmetric 6F-dianhydride and 3,4'-(methylene)diphthalic anhydride from asymmetric benzophenone dianhydride and compounds comprising the same.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIG. 1 shows a schematic outline of the step-by-step synthesis of asymmetric 3,4'-(hexafluroisopropylidene) diphthalic anhydride (a-6FDA) and asymmetric 3,4'-(methylene)diphthalic anhydride (a-MDPA) from asymmetric 2,3,3',4'-benzophenone dianhydride (a-BTDA)

DETAILED DESCRIPTION

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

Conventional polyimides prepared from commercially available symmetric dianhydrides display very high melt viscosity and are, thus, unsuitable for certain applications, such as resin transfer molding (RTM), vacuum assisted RTM (VARTM) or resin film infusion (RFI) processing.

There is a need for polyimides that are suitable for higher temperature aerospace applications and for low cost processing. The higher temperature applications for polyimides include lightweight composites for civil and military aircraft components, and often require temperatures above 315° C. as the aircraft engines continue to demand higher performance capability.

Polyimides derived from asymmetric aromatic dianhydrides display unique properties that possess advantages over polyimides made from conventional commercial symmetric dianhydrides. Namely, polyimides derived from asymmetric dianhydrides exhibit lower melt-viscosities which impart better processability as well as high temperature capability. These characteristics are especially advantageous for aerospace composite fabrication such as resin transfer molding (RTM), vacuum assisted RTM (VARTM), and resin film infusion (RFI) in the manufacturing of aircraft engine components. Currently, commercially available symmetric 6F-dianhydride produces polyimides with the best high temperature performance compared to other symmetric dianhydrides. However, there is a need to produce asymmetric 6F-dianhydride that is expected to yield polyimides with higher temperature capability as well as easy processing.

The present innovation includes new synthetic routes of using asymmetric benzophenone dianhydride (a-BTDA) to make asymmetric 6F-dianhydride (a-6FDA) and a-MDPA capable of producing higher performance composite parts by RTM, VARTM, and RFI manufacturing methods. The asymmetric structures of a-6FDA and a-MDPA can contribute to lower the melt viscosities towards the corresponding polyimides due to irregular packing of the resultant polyimides. The lower melt viscosity enables easier fabrication of high quality large composite structures with low voids by resin transfer molding (RTM), VARTM, or resin film infusion (RFD.

In one embodiment, the a-6FDA and/or a-MDPA can be used in RTM, VARTM, and RFI processing to make composite structures for aircraft engine components and airframe structures by injection or infusion of low melt-viscosity polyimide resins into carbon fiber preforms instead of carbon fiber prepreg lay-up.

According to an aspect, the innovation provides new synthetic routes to prepare asymmetric 6F-dianhydride (a-6FDA) and 3,4'-(methylene) diphthalic anhydride (a-MDPA) from asymmetric benzophenone (a-BTDA) which has been made available by custom synthesis. This innovation can simplify synthetic strategies for practical, large scale production. Once a-6FDA and a-MDPA are conveniently available, it will be feasible to formulate and produce the corresponding polyimides for high temperature applications above 315° C.

According to an aspect, the innovation provides new synthetic routes of converting asymmetric 2,3,3',4'-bezophenone dianhydride (a-BTDA) into 3,4'-(hexafluroisopropylidene)diphthalic anhydride (a-6FDA) and 3,4'-(methylene) diphthalic anhydride (a-MDPA) via the synthetic schemes described herein.

In one embodiment, the resulting a-6FDA and a-MDPA may be used to create polyimide resins for applications in resin transfer molding (RTM), VARTM, and resin film infusion (RFI) for aerospace applications. The polyimide resins prepared from a-6FDA and a-MDPA are expected to have lower melt-viscosity and higher temperature performance than the polyimides derived from conventional symmetric dianhydrides.

In an aspect of the innovation, asymmetric benzophenone can be converted to the corresponding bisimide by reacting the asymmetric benzophenone with an aromatic or aliphatic amine as a precursor for the synthesis of a-6FDA and a-MDPA.

In one embodiment, the synthetic pathway may comprise producing asymmetric 6F-dianhydride and asymmetric 3,4'-(methylene)diphthalic anhydride as set forth in FIG. 1.

According to an example embodiment of the innovation, asymmetric 6F-dianhydride may be made by adding a first $CF_3$ group to the carbonyl unit of the bisimides of a-BTDA (1) or (1a) by reacting trimethyl(trifluoromethyl)silane and suitable catalysts, followed by acidification to produce intermediate (2), which can be further converted into corresponding halides via treatment with HX (where X is selected from Cl, Br, or I) to afford intermediate (3). The second $CF_3$ group can be added by reacting (3) with $CF_3Br$ or $CF_3I$ to afford the bisimides of 6F-dianhydride (4), which can be hydrolyzed with sodium hydroxide to form the corresponding sodium salts of 6F-tetracarboxylic acid, followed by acidification by HCl to yield 6F-tetracarboxylic acid (5). Subsequent cyclodehydration of 6F-tetracarboxylic acid (5) either by thermal dehydration at 250-300° C. or by chemical dehydration using acetic anhydride afford a-6FDA (6). Suitable catalysts for trifluoromethylation of carbonyl unit include, but are not limited to trimethylamine N-oxide, $K_2CO_3$, $Li_2CO_3$, tetrabutyl ammonium fluoride, etc.

Asymmetric 3,4'-(methylene)diphthalic anhydride (a-MDPA) may be made by reducing the carbonyl group within the bisimides of asymmetric benzophenone dianhydride (a-BTDA) followed by the hydrolysis and cyclodehydration to afford a-MDPA.

In one embodiment, either a-6FDA or a-MDPA can then react with a diamine, especially an aromatic diamine, to produce polyimide resins with low melt viscosity.

Example 1: Preparation of a-BTDA N-methyl bisimide

To a 500 ml three-necked flask equipped with a condenser and a Dean-Stark trap, 32.2 gm (0.1 mole) of 2,3,3',4'-benzophenone dianhydride (a-BTDA) and 200 ml of N,N-dimethylformamide (DMF) were added, and the mixture was stirred at room temperature until a-BTDA dissolved. The reaction mixture was cooled to 0° C. and 40% aqueous methylamine (26 ml) was added dropwise vis a dropping funnel in 20 min. and then heated to reflux while the azeotrope water was removed through the Dean-stark trap overnight. The reaction mixture was concentrated in a rotary evaporator to remove DMF, and the solid precipitated out was collected to afford 34 gm (98%) of the a-BTDA N-methyl bisimide (1).

Example 2: Preparation of a-BTDA N-phenyl bisimide

A solution of 32.2 gm (0.1 mole) of a-BTDA and 20.4 gm (0.22 mole) of aniline in 100 ml of dioxane were heated to reflux overnight in a 500 ml of flask equipped with a condenser. The reaction mixture was cooled to room temperature and the resultant solid precipitated out was collected as the first crop. Further evaporation of dioxane produces a second crop. The combination of two crops afforded 45 gm (95% yield) of a-BTDA N-phenyl bisimide (1a).

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of making bisimide of asymmetric benzophenone dianhydride comprising reacting asymmetric benzophenone dianhydride (a-BTDA) with an aromatic or aliphatic amine to produce a bisimide of a-BTDA having the structure depicted below:

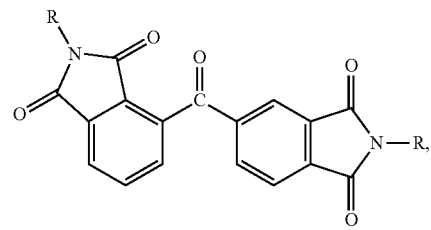

wherein R is independently selected from phenyl, $CH_3$, or $C_2H_5$, wherein the bisimide of a-BTDA is a precursor for the synthesis of a-6FDA and a-MDPA.

2. The method of claim 1 further comprising:
adding a first trifluoromethyl group ($CF_3$) via reaction with trimethy(trifluoromethyl)silane and a catalyst to a carbonyl unit of the bisimide of a-BTDA to form a first intermediate;
converting an alcohol group of the first intermediate into a halide via treatment with HX, wherein X is selected from Cl, Br, or I, to form a second intermediate;
adding second trifluoromethyl group ($CF_3$) through reaction with $CF_3Br$ or $CF_3I$ to produce a bisimide of a-6FDA, wherein the bisimide of a-6FDA has the following structure:

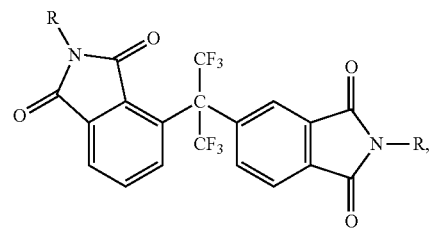

wherein R is independently selected from phenyl, $CH_3$, or $C_2H_5$.

3. The method of claim 2 further comprising:

hydrolyzing the bisimide of a-6FDA by sodium hydroxide (NaOH) to obtain sodium salts of a-6F tetracarboxylic acid; and acidifying the sodium salts of a-6F tetracarboxylic acid by HCl to obtain an asymmetric 6F-tetracarboxylic acid having the following structure:

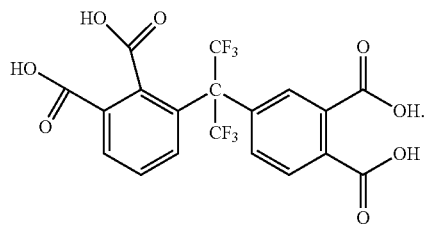 [SMILES: O=C(O)c1ccc(C(c2cccc(C(=O)O)c2C(=O)O)(C(F)(F)F)C(F)(F)F)cc1C(=O)O]

4. The method of claim 3 wherein the asymmetric 6F-tetracarboxylic acid is thermally imidized by heating to about 250-300° C. to obtain a-6FDA having the structure depicted below:

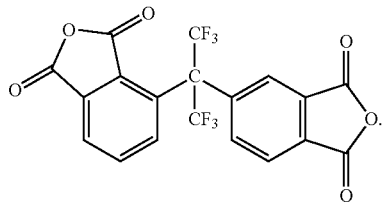 [SMILES: O=C1OC(=O)c2cc(C(c3cccc4c3C(=O)OC4=O)(C(F)(F)F)C(F)(F)F)ccc21]

5. The method claim of 3 wherein the asymmetric 6F-tetracarboxylic acid is chemical imidized by acetic anhydride to obtain a-6FDA.

6. The method of claim 1 further comprising reducing a carbonyl unit of the bisimide of a-BTDA to the methylene unit to obtain a bisimide of asymmetric (methylene)diphthalic anhydride (a-MDPA) having the structure depicted below:

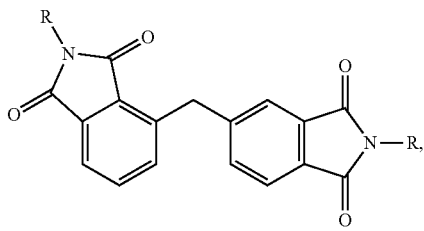

wherein R is independently selected from phenyl, CH$_3$, or C$_2$H$_5$.

7. The method of claim 6 further comprising:

hydrolyzing the bisimide of asymmetric (methylene)diphthalic anhydride (a-MDPA) by sodium hydroxide to obtain sodium salts of asymmetric methylene tetracarboxylic acid; and acidifying the sodium salts of asymmetric methylene tetracarboxylic acid by HCl to obtain asymmetric methylene tetracarboxylic acid having the following structure:

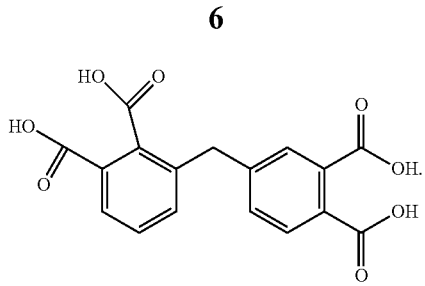

8. The method of claim 7 wherein the asymmetric tetracarboxylic acid is thermally imidized at about 250-300° C. to obtain 3,4'-(methylene)diphthalic anhydride (a-MDPA) having the following structure:

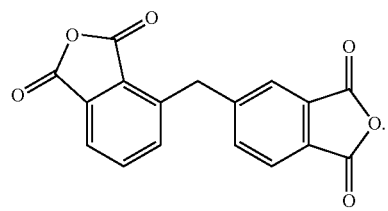 [SMILES: O=C1OC(=O)c2cc(Cc3cccc4c3C(=O)OC4=O)ccc21]

9. The method of claim 7 wherein the asymmetric tetracarboxylic acid is chemical imidized by acetic anhydride to obtain 3,4'-(methylene)diphthalic anhydride (a-MDPA).

10. A method of making asymmetric 3, 4'-(hexafluroisopropylidene)diphthalic anhydride (a-6FDA) comprising:

reacting asymmetric benzophenone dianhydride (a-BTDA) with an aromatic or aliphatic amine to produce a bisimide of a-BTDA having the structure depicted below:

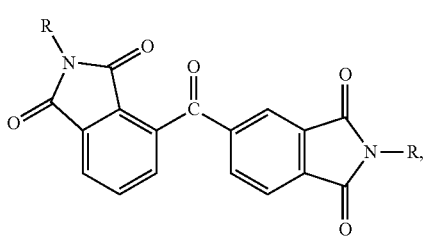

wherein R is independently selected from phenyl, CH$_3$, or C$_2$H$_5$;

adding a first trifluoromethyl group (CF$_3$) via reaction with trimethy(trifluoromethyl)silane to a carbonyl unit of the bisimide of a-BTDA to form a first intermediate;

converting an alcohol group of the first intermediate into a halide via treatment with HX, wherein X is selected from Cl, Br, or I, to form a second intermediate;

adding second trifluoromethyl group (CF$_3$) through reaction with CF$_3$Br or CF$_3$I to produce a bisimide of a-6FDA, wherein the bisimide of a-6FDA has the following structure:

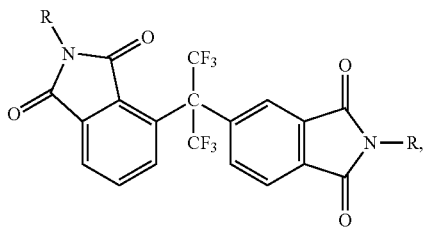

wherein R is independently selected from phenyl, CH$_3$, or C$_2$H$_5$.

11. The method of claim 10 further comprising:
hydrolyzing the bisimide of a-6FDA to obtain sodium salts of a-6F tetracarboxylic acid; and acidifying the sodium salts of a-6F tetracarboxylic acid to obtain an asymmetric 6F-tetracarboxylic acid having the following structure:

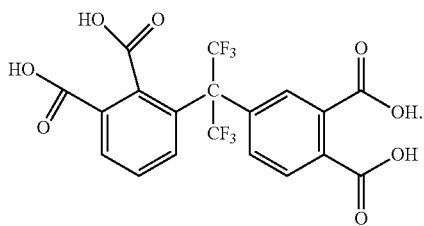 [SMILES: O=C(O)c1ccc(C(c2cccc(C(=O)O)c2C(=O)O)(C(F)(F)F)C(F)(F)F)cc1C(=O)O]

12. The method of claim 11, wherein the bisimide of a-6FDA is hydrolyzed by sodium hydroxide (NaOH).

13. The method of claim 11, wherein the sodium salts of a-6F tetracarboxylic acid are acidified by HCl.

14. The method of claim 11 wherein the asymmetric 6F-tetracarboxylic acid is thermally imidized by heating to about 250-300° C. to obtain a-6FDA, having the structure depicted below:

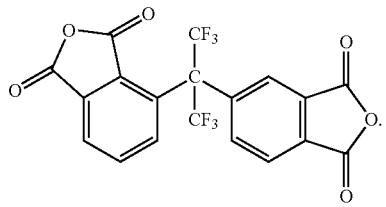 [SMILES: O=C1OC(=O)c2cc(C(c3cccc4c3C(=O)OC4=O)(C(F)(F)F)C(F)(F)F)ccc21]

15. The method claim of 11 wherein the asymmetric 6F-tetracarboxylic acid is chemical imidized by acetic anhydride to obtain a-6FDA.

16. A method of making asymmetric 3,4'-(methylene) diphthalic anhydride (a-MDPA) comprising:
reacting asymmetric benzophenone dianhydride (a-BTDA) with an aromatic or aliphatic amine to produce a bisimide of a-BTDA having the structure depicted below:

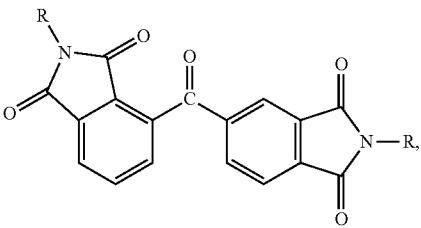

wherein R is independently selected from phenyl, CH$_3$, or C$_2$H$_5$;
reducing a carbonyl unit of the bisimide of a-BTDA to a methylene unit to obtain a bisimide of asymmetric (methylene)diphthalic anhydride (a-MDPA); and
hydrolyzing the bisimide of asymmetric (methylene)diphthalic anhydride (a-MDPA) to obtain sodium salts of asymmetric methylene tetracarboxylic acid; and
acidifying the sodium salts of asymmetric methylene tetracarboxylic acid to obtain asymmetric methylene tetracarboxylic acid having the following structure:

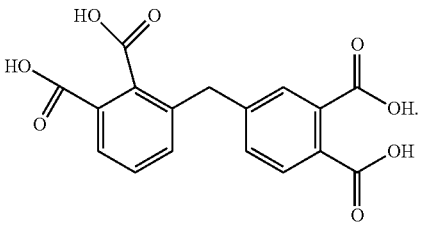 [SMILES: O=C(O)c1ccc(Cc2cccc(C(=O)O)c2C(=O)O)cc1C(=O)O]

17. The method of claim 16, wherein the bisimide of asymmetric (methylene)diphthalic anhydride is hydrolyzed by sodium hydroxide (NaOH).

18. The method of claim 16, wherein the sodium salts of asymmetric methylene tetracarboxylic acid are acidified by HCl.

19. The method of claim 16 wherein the asymmetric tetracarboxylic acid is thermally imidized at about 250-300° C. to obtain 3,4'-(methylene)diphthalic anhydride (a-MDPA), having the following structure:

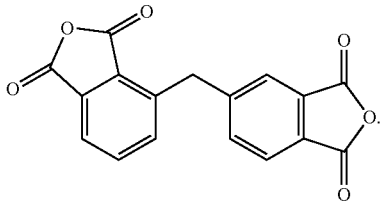 [SMILES: O=C1OC(=O)c2cc(Cc3cccc4c3C(=O)OC4=O)ccc21]

20. The method of claim 16, wherein the asymmetric tetracarboxylic acid is chemical imidized by acetic anhydride to obtain 3,4'-(methylene)diphthalic anhydride (a-MDPA).

* * * * *